United States Patent [19]

Sidot et al.

[11] Patent Number: 5,095,128

[45] Date of Patent: Mar. 10, 1992

[54] PREPARATION PROCESS FOR PIPERONAL

[75] Inventors: Christian Sidot, Ezanville; Yani Christidis, Paris, both of France

[73] Assignee: Societe Francaise Hoechst, Puteaux, France

[21] Appl. No.: 608,450

[22] Filed: Nov. 2, 1990

[30] Foreign Application Priority Data

Nov. 2, 1989 [FR] France ................ 89 14358

[51] Int. Cl.⁵ ........................................ C07D 317/54
[52] U.S. Cl. .................................................. 549/436
[58] Field of Search ........................................ 549/436

[56] References Cited

U.S. PATENT DOCUMENTS 4,218,380  8/1980  Fiege et al. .................. 549/436

OTHER PUBLICATIONS

Chemical Abstracts, vol. 112, 1990, p. 700, resume No. 55145n, Columbus, Ohio, USA; L. Cerveny et al. Synthesis of Heliotropin, & Perfum. Flavor. 1989, 14 (12), 13-14, 16-18.

Primary Examiner—Nicky Chan
Attorney, Agent, or Firm—Browdy and Neimark

[57] ABSTRACT

Preparation process for piperonal by decarboxylating oxidation of 3,4-methylenedioxy mandelic acid by nitric acid in aqueous medium in the presence of hydrochloric acid.

10 Claims, No Drawings

PREPARATION PROCESS FOR PIPERONAL

The present invention relates to a preparation process for piperonal.

Piperonal, known in the perfume industry under the name heliotropin, can be obtained either by heating protocatechualdehyde with potash and methylene iodide, or by applying the Sommelet reaction to piperonyl chloride, or by oxidizing piperic acid, safrole or preferably isosafrole with potassium permanganate or ozone, or finally by decarboxylating oxidation of 3,4-methylenedioxy mandelic acid with a silver benzoate-iodine complex under reflux with benzene. (Beilstein, 19, 115, 119, I 660–662, II, 141–143, and P. S. Raman Current Science, 1958, 27, 22).

It is known that hydroxylated alpha carboxylic acids can be broken down into their corresponding carbonyl derivative either by simple heating, or by the action of sulphuric acid, or by oxidation. The thermolysis is especially applicable to fatty acids with a lactide intermediate formation. The sulphuric cleaving appears to be limited to citric and mellic acids. As regards oxidizing scissions, they generally require iodine or its complexes as in the case of the breaking down of mandelic acid into benzaldehyde (Annales, 1926, 446, 71) or of 3,4-methylenedioxy mandelic acid into piperonal (P. S. Raman, loc. cit.) or oxidizing agents adapted to cleaving vicinal functional groups such as lead tetraacetate.

Therefore it is noted that known processes for obtaining piperonal are not economically satisfactory due to the use of expensive reagents or raw materials or the implementation of reactions which are difficult to extrapolate on an industrial scale. Faced with an ever greater demand for pure heliotropin, it was thus necessary to be able to have available an economical industrial process for obtaining it.

Now the Applicant has just discovered a new process for obtaining piperonal easily and with good yields starting with 3,4-methylenedioxy mandelic acid. The process of the present invention consists of breaking down 3,4-methylenedioxy mandelic acid into piperonal by nitric oxidation and is characterized in that the oxidation is carried out in aqueous medium in the presence of hydrochloric acid. The hydrochloric acid accelerates and above all allows the speed of decarboxylating oxidation of the 3,4-methylenedioxy mandelic acid by the nitric acid to be very easily regulated. Advantageously, between 1 and 2 moles of hydrochloric acid per mole of 3,4-methylenedioxy mandelic acid employed are used.

The quantity of nitric acid employed is preferably close to the stoichiometric quantity, that is to say close to 0.66 mole of nitric acid per mole of 3,4-methylenedioxy mandelic acid employed. Notably, a slight excess of nitric acid is added. About 0.8 mole of nitric acid per mole of 3,4-methylenedioxy mandelic acid is used.

The nitric acid is commercially available nitric acid of a concentration of between 65% and 69% and it is introduced slowly, as required by the rate at which it is consumed, into an aqueous suspension of 3,4-methylenedioxy mandelic acid.

The decarboxylating oxidation is exothermic, so that speed of introduction of the nitric acid into the aqueous suspension of 3,4-methylenedioxy mandelic acid is regulated in such a way as to maintain the desired temperature without using external heating or cooling.

In order to facilitate the start of the oxidation reaction, it is sometimes advantageous to introduce a very small quantity of sodium nitrite into the reaction medium. In this case, 1 mmole of sodium nitrite can be used per mole of 3,4-methylenedioxymandelic acid employed.

The process according to the present invention is advantageously carried out at temperature of between ambient temperature and 50° C., preferably between 40° and 50° C., and it takes place in an aqueous medium. Given that 3,4-methylenedioxy mandelic acid as well as piperonal are products which are only slightly soluble in water, the process according to the invention is carried out generally in a heterogeneous phase. At the end of the reaction, the piperonal formed is isolated from the reaction medium by methods known per se. Advantageously, it is extracted using a compatible solvent which is non-miscible in water, then, if necessary, it is purified either by distillation under reduced pressure or by recrystallization from ethanol at 70% in water.

The following example illustrates the present invention without however limiting it.

EXAMPLE

The following are mixed together under agitation at ambient temperature:

294.23 g (1.5 mole) of 3,4-methylenedioxy mandelic acid;
562 g of water;
258.75 g of 37% hydrochloric acid being 2.625 moles;
2.1 g of 69% nitric acid being 23 mmoles.

The suspension obtained is heated under agitation at 43°±2° C., then 103.5 mg (1.5 mmole) of sodium nitrite dissolved in 4 g of water is introduced rapidly at this temperature, then 107.5 g of 69% nitric acid, being 1.177 mole, is introduced slowly, over about three hours, in such a way so that the temperature of the reaction medium is maintained at between 40° and 50° C. without using external heating or cooling. At the end of the introduction, the reaction medium is left for one our under agitation at 43°±2° C., then it is cooled down to ambient temperature and finally extraction takes place three times with 600 g of trichloro-1,1,1-ethane. The re-united organic phases are then washed successively, once with water, three times with a saturated aqueous solution of sodium hydrogen carbonate and finally once with water before being concentrated under reduced pressure.

Thus 220 g (1.46 mole) of crude piperonal is isolated which is purified by distillation under reduced pressure.

Thus 178 g (1.186 mole) of pure piperonal is isolated distilling at 106° C. under a vacuum of 2.4 mbars and having a melting point of 37°+1° C. The yield is established at 79% of the theoretically calculated value relative to the 3,4-methylenedioxy mandelic acid used.

What is claimed is:

1. Preparation process for piperonal by nitric oxidation of 3,4-methylenedioxy mandelic acid in aqueous medium, characterized in that the oxydation is carried out in the presence of hydrochloric acid.

2. Process according to claim 1, characterized in that about a stoichiometric quantity of nitric acid is used.

3. Process according to claim 1, characterized in that it is carried out at a temperature between ambient temperature and 50° C.

4. Process according to claim 1, characterized in that it is carried out in a heterogeneous phase.

5. Process according to claim 2, characterized in that it is carried out at a temperature between ambient temperature and 50° C.

6. Process according to claim 2, characterized in that it is carried out in a heterogeneous phase.

7. Process according to claim 3, characterized in that it is carried out in a heterogeneous phase.

8. A process for the preparation of piperonal comprising oxidizing 3,4-methylenedioxy mandelic acid with nitric acid in an aqueous medium in the presence of hydrochloric acid, said hydrochloric acid being present in an amount between 1 and 2 moles per mole of 3,4-methylenedioxy mandelic acid, and said nitric acid being employed in a small excess of the stoichiometric quantity.

9. A process according to claim 8, wherein said nitric acid is introduced slowly into an aqueous suspension of said 3,4-methylenedioxy mandelic acid.

10. A process according to claim 8, further comprising introducing a small quantity of sodium nitrate into the reaction medium.

* * * * *